United States Patent [19]

Miller et al.

[11] Patent Number: 5,034,194
[45] Date of Patent: Jul. 23, 1991

[54] WINDOWLESS FLOW CELL AND MIXING CHAMBER

[75] Inventors: Robert J. Miller, Burlingame, Calif.; James D. Ingle, Corvallis, Oreg.

[73] Assignee: Oregon State University, Corvallis, Oreg.

[21] Appl. No.: 152,012

[22] Filed: Feb. 3, 1988

[51] Int. Cl.⁵ ............................................... B01L 3/00
[52] U.S. Cl. ...................... 422/99; 422/102; 422/104; 422/58; 436/165; 436/172; 436/909; 356/440; 250/576
[58] Field of Search ............... 422/99, 102, 104, 55, 422/58, 68; 436/164, 165, 172, 909; 356/246, 440 X; 250/576 X

[56] References Cited

U.S. PATENT DOCUMENTS

| | | | |
|---|---|---|---|
| 4,643,570 | 2/1987 | Mächler et al. | 250/576 X |
| 4,643,580 | 2/1987 | Gross et al. | 250/576 X |
| 4,734,260 | 3/1988 | Lautenschläger | 436/165 X |

Primary Examiner—Robert J. Warden
Assistant Examiner—Lynn M. Kummert
Attorney, Agent, or Firm—Klarquist, Sparkman, Campbell, Leigh & Whinston

[57] ABSTRACT

A windowless flow cell for detecting substances in a flowing fluid stream by chemiluminescence, fluorescence or absorption in flow injection analysis schemes, liquid chromatographs, or gas chromatographs is described. Furthermore, the mixing characteristics of the invention suggest its use as a micro-volume mixing chamber for a variety of experiments.

A windowless flow cell comprising an upper body plate, upper wire spacer, mid-body plate, lower body spacer plate, and lower body plate interconnected by anchor bolts is described. Cell wires are attached to the upper body plate and the lower body plate. A primary reagent port through the upper body plate, with secondary reagent port and tertiary reagent port through the mid-body plate provide the fluids to be mixed. A thin film of the mixture of fluids to be examined flows down the cell wires through the examining chamber and through the drop detector and overflow detector prior to exiting the drain port by way of a low vacuum source.

A micro-volume mixing chamber comprising a plexiglass mainframe with viewing windows of an examining chamber into which a plurality of reagent ports flow to form a fluid film on cell wires is described. The examining chamber also comprises gas inlet ports for control of pressure and of the type of gas environment.

18 Claims, 3 Drawing Sheets

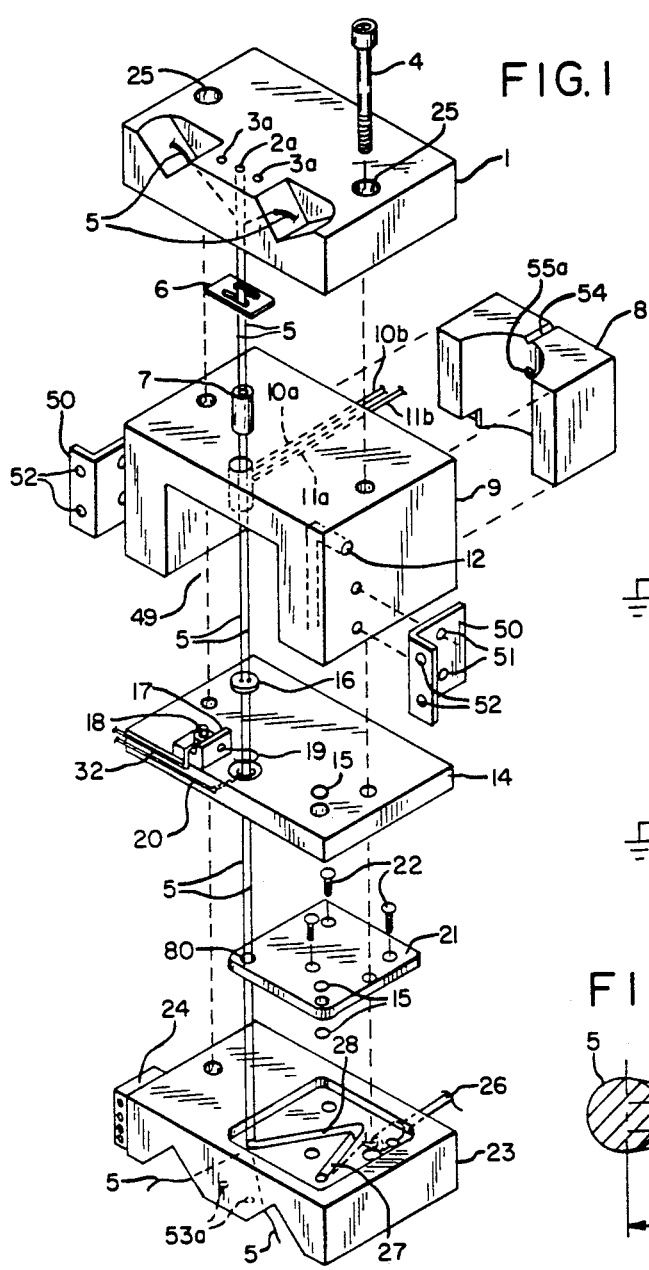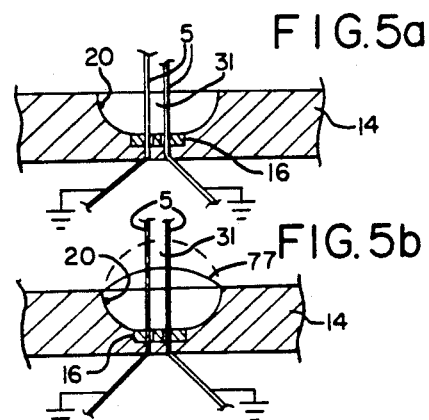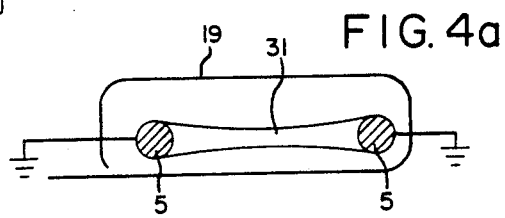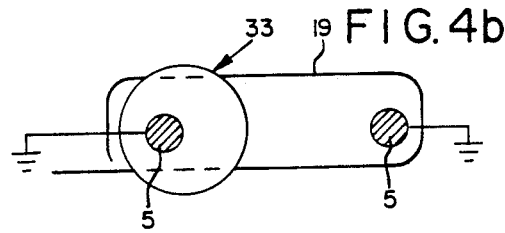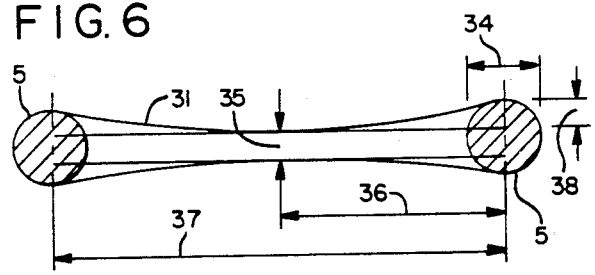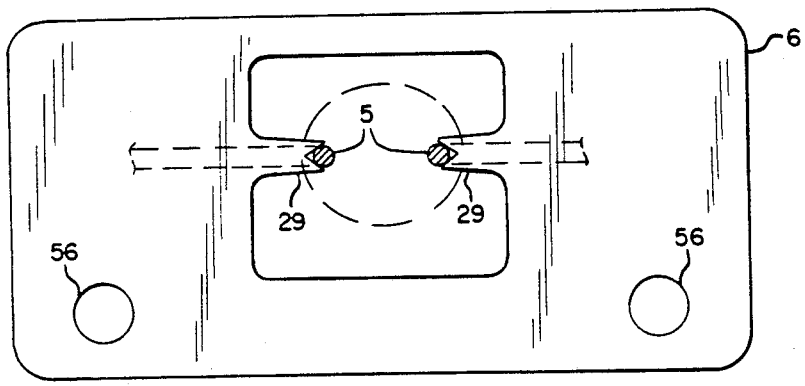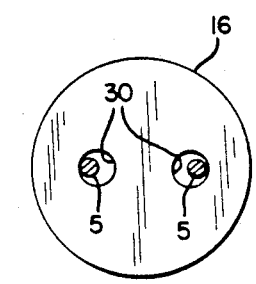

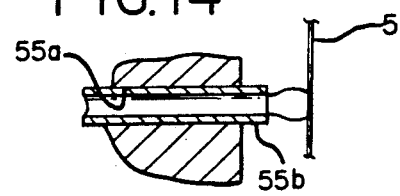
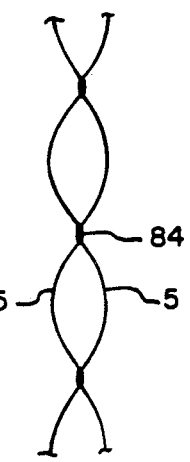
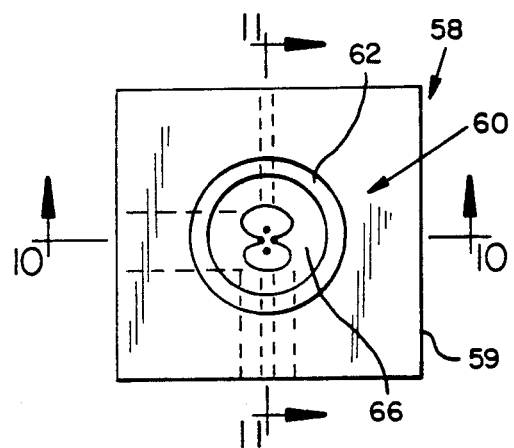
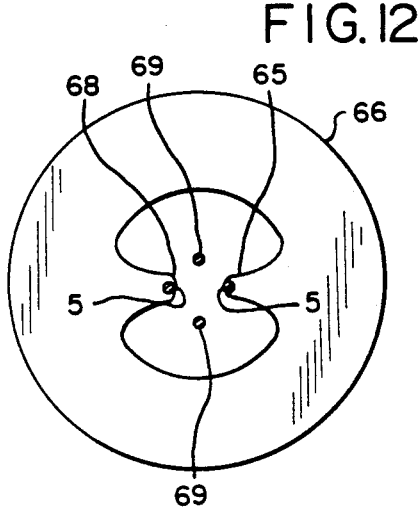
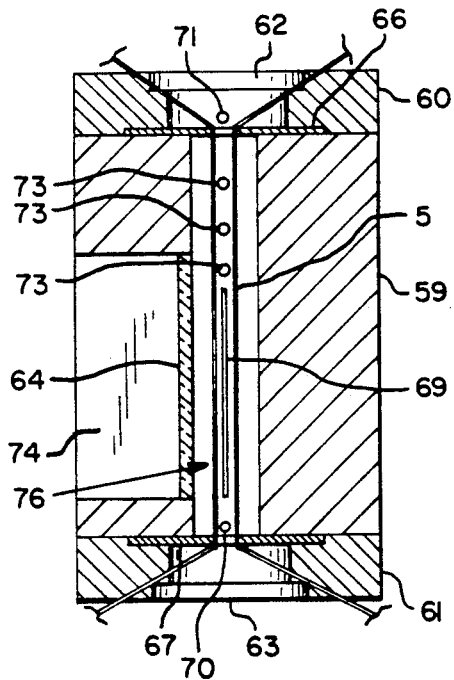
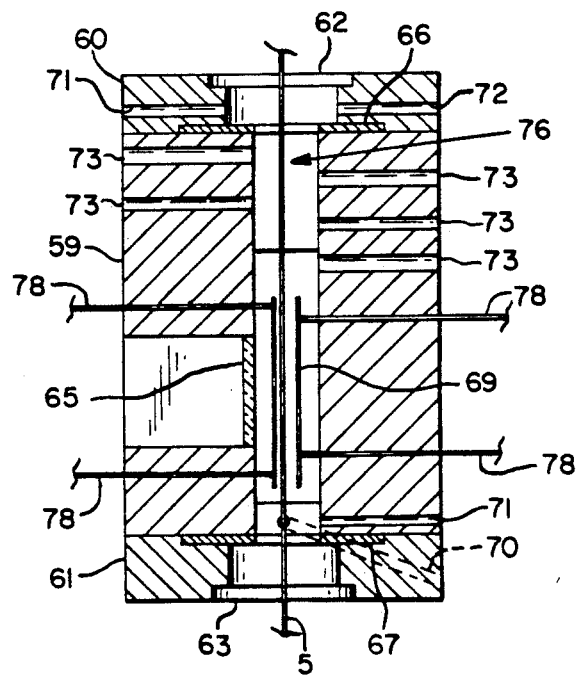

WINDOWLESS FLOW CELL AND MIXING CHAMBER

BACKGROUND OF THE INVENTION

This invention is a further development in sample flow cells and mixing chamber for the detection and rapid mixing of substances in a flowing stream.

Some sample flow cells in the past have had problems with light from an excitation source. See, for example, U.S. Pat. No. 4,037,974, which provides for an opaque mask and/or specially designed sample flow cell with coating material to reduce the problem of light from an excitation source. Furthermore, sampling of small flow volume has presented some difficulties with the unwanted introduction of air bubbles. See, for example, U.S. Pat. No. 4,074,940. Another problem arises in having sufficient fluorescence quantum yield for adequate detection which can be solved by a method and apparatus using a stationary phase for sampling as shown in U.S. Pat. No. 4,181,853.

Windowless flow cells by design minimize scattered light. Two previous designs for windowless spectroscopic flow cells have been reported. One design is based upon the suspension of the flowing stream between an outlet capillary tube and a small diameter rod placed directly below the outlet tube. A stationary, but constantly replenished four microliter droplet is formed in the gap between the tube and the rod. The second design is based on directing the flowing stream from a capillary tube across the gap to another capillary tube. The effluent stream is confined by sheathing with a flowing solvent to provide a windowless optical volume of 0.006 to 0.15 microliters. Diebold, G. J.; Zare, R. N., Science, 1977, 196, 1439-41 and Herschberger, L. W.; Callis, J. B.; Christian, G. D., Anal. Chem., 1979, 51, 1444-1446.

SUMMARY OF THE INVENTION

It is an object to provide the ability to mix rapidly two or more streams through the interaction of a falling film with one or more jet streams within the optically viewed area.

It is another object of this invention to provide an apparatus which avoids the interaction of the probing or probed light beam with optical materials which cause undesirable effects such as reflection, scattering, absorption, and background fluorescence.

It is a further object to eliminate sorption of substances in the flowing stream onto container walls or desorption of substances from the container walls into the flowing stream.

It is another further object to provide very small optical dead volumes to achieve resolution of two or more substances contained in two or more small volume elements separated in time in a flowing stream.

A further object is to provide a flowing stream as a supported film rather than an unsupported cylindrical stream.

Another further object is to provide an optically thin media useful for the detection of highly absorbing substances and for minimization of undesired absorption effects in luminescence measurements.

A final object is to provide the ability to study time resolved behavior by probing different vertical sections of the falling film.

According to the invention, we provide an upper body plate within which is provided a primary reagent port along with the cell wires which pass through and are mounted on the upper wire spacer, the mid-body plate, lower body spacer plate, and the lower body plate. Secondary and tertiary reagent ports are provided. A low vacuum source removes the effluent through a drain port in the lower body plate. A drop detector and overflow detector are mounted on the lower body spacer plate. Appropriately designed electronic equipment detects problems in the formation of the film through processing of the drop detector probes and the overflow detector probes. The windowless flow cell is suitable for the detection of species directly by chemiluminescence, fluorescence or absorption base measurements such as in a flow injection analysis scheme. Versatility also allows direct interfacing to a liquid chromatograph or to the effluent from a gas chromatograph.

Furthermore, the mixing characteristics of the properly designed invention suggest its use as a micro-volume mixing chamber for a variety of experiments. In this embodiment, a plexiglass mainframe contains viewing windows above, below and on the side of the examining chamber. A plurality of reagent ports with properly adjusted reagent tubes to cell wires spacing form a pulsing fluid film. Mixing aids comprise two wires positioned perpendicular to the flowing fluid film. Another embodiment uses two cell wires in helical form where the carefully designed nodes of each cell wire are joined. A capillary tube is used to transfer the mixed fluid from the cell wire film supports to another location. The enclosed examining chamber also comprises a gas inlet and gas outlet for control of the pressure and the type of gas environment.

Furthermore, the preferred embodiment of the windowless flow cell and micro-volume mixing chamber allows for the return of the falling film to a tube confined plug flow (i.e. first in, first out). The tube confined plug flow is accomplished by butting a wettable reagent tube directly against the falling film supports. A return to plug flow is desirable when the windowless flow cell or micro-volume mixing chamber is located up-stream from any subsequent detecting or fraction collecting instrumentation.

BRIEF DESCRIPTION OF THE DRAWINGS

FIG. 1 is an exploded perspective view of the windowless flow cell.

FIG. 2 is a top view of the upper wire spacer.

FIG. 3 is a top view of the lower wire spacer.

FIG. 4a is a top sectional view of the film with drop detector probes.

FIG. 4b is a top cross sectional view of a drop in contact with the drop detector probes.

FIG. 5a is a front cross sectional view of the overflow detector probes.

FIG. 5b is a front cross sectional view with liquid in contact with the overflow detector probes.

FIG. 6 is a detailed cross sectional view of the film.

FIG. 9 is a top view of the micro-volume mixing chamber.

FIG. 10 is a front cross sectional view of the mixing chamber along lines 10—10 of FIG. 9.

FIG. 11 is a cross sectional side view of the mixing chamber along lines 11—11 of FIG. 9.

FIG. 12 is a top enlarged view of the wire spacer.

FIG. 13 is a perspective view of helical cell wires.

FIG. 14 shows the spacing between a tube and cell wires with the pulsing fluid.

DESCRIPTION OF THE PREFERRED EMBODIMENT

Figure 7:
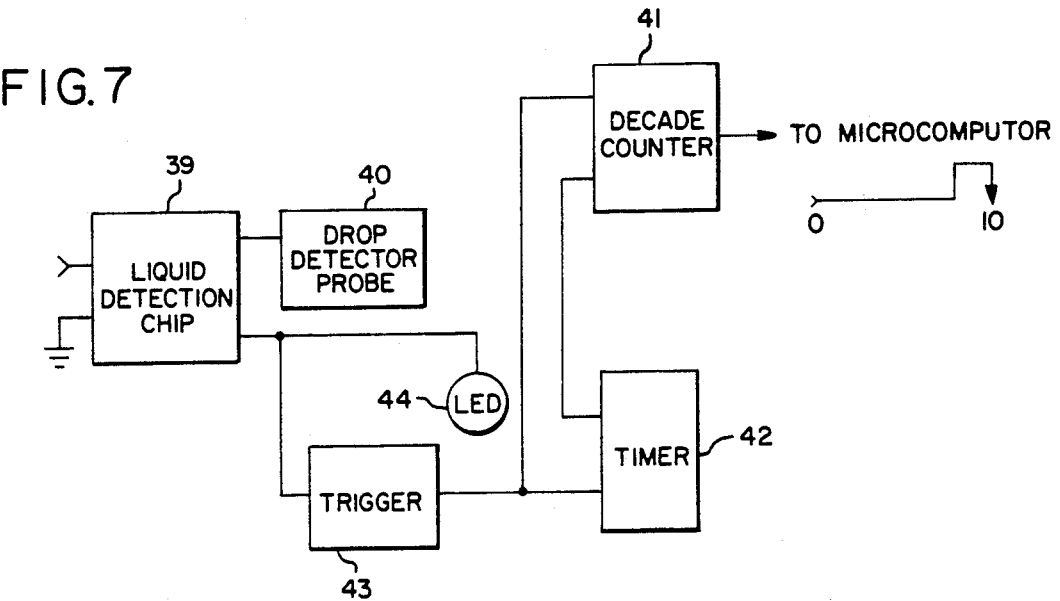
FIG. 7 is a block circuit diagram of the drop detector probe.

FIG. 1 shows an exploded view of the windowless flow cell which is physically constructed with an upper body plate 1, a mid-body plate 9 into which slides a mirror block 8, a lower body spacer plate 14, and a lower body plate 23. Anchor bolts 4 attach the upper body plate 1, the mid-body plate 9, the lower body spacer plate 14, and the lower body plate 23 together through anchor bolt holes 25. Cell wires 5 are firmly positioned in the upper body plate 1 by upper body cell wire set screws 3b (not shown) in upper body set screw holes 3a. The cell wires 5 are further positioned in the upper wire spacer 6 before passing through the mid-body plate 9 within the teflon insert 7. The cell wires 5 continue through the examining chamber 49, the drop detector probe 19, and the overflow detector probe 20. Within the lower body spacer plate 14 is the lower wire spacer 16 through which the cell wires 5 pass. The cell wires 5 then pass through cell wire hole 80 of the drain cavity cover 21 and the drain cavity 28 until fixed by lower body cell wire set screws (not shown) operating through lower body set screw holes 53a in lower body plate 23.

Fluid flow along the cell wires 5 is initiated through the primary reagent port 2a by a primary reagent tube (not shown). Secondary reagent port 10a is located through mid-body plate 9 and through insert 7. Secondary reagent tube 10b is positioned within secondary reagent port 10a until "near the cell wires" 5. Where "near the cell wires" refers to a carefully adjusted cell wire to reagent tube spacing. The distance corresponds to approximately 80% of the period of the emerging jet stream. When properly adjusted, the falling film will rapidly pulsate. Tertiary reagent port 11a is located within the mid-body plate 9 and directly below secondary reagent port 10a. Tertiary reagent port 11a runs through the mid-body plate 9 also penetrating teflon insert 7. Tertiary reagent tube 11b is positioned within tertiary reagent port 11a until "near cell wires" 5. Analyte reagent port 54 is located in mirror block 8. Auxilary port 55a is located in the center of mirror block 8 which corresponds to the geometric center of the examining chamber 49. Similarly analyte reagent tube (not shown) and auxilary tube 55b (see FIG. 14) are appropriately positioned "near cell wires" 5. When utilizing any port other than the primary, flow must be initiated in each of these ports prior to the introduction of a flow from the primary port. Air inlet port 12 is cut within mid-body plate 9 through the lower body spacer plate 14 with the accompanying o-rings 15 and through drain cavity cover 21 to the air inlet cavity 27. Fluid flow originating from the primary reagent tube (not shown), the secondary reagent tube 10b, and the tertiary reagent tube 11b flow to the drain cavity 28 located in the lower body plate 23. Drain cavity 28 and air inlet cavity 27 join at drain port 26 to exit from the flow cell. Drain port 26 is attached to a low vacuum source (not shown).

Drain cavity cover 21 is attached to lower body plate 23 by drain cavity cover screws 22. Mounting brackets 50 are attached to mid-body plate 9 by means of bracket attachment screw holes 51. Mounting brackets 50 can also be attached to other instruments by means of flow cell attachment screw holes 52. Cell probe block 17 is mounted to the lower body spacer plate 14 by means of mounting screw 18. Drop detector probe 19 and overflow detector probe 20 and probe wires 32 are configured around cell wires 5 and lead to four wire connectors 24 for appropriate electronic attachments.

FIG. 2 is an enlargement of upper wire spacer 6 with spacer screw holes 56. The cell wires 5 are held in place by upper wire spacer prongs 29. The upper body plate 1 is machined to receive upper wire spacer 6. Primary reagent tube 2b rests on cell wires 5 close to upper wire spacer 6.

FIG. 3 is an enlarged view of lower wire spacer 16 showing two clearance holes 30 through which the cell wires 5 pass.

FIG. 4a shows the film 31 held by grounded cell wires 5 and encircled by drop detector probe 19.

In FIG. 4b, a drop 33 has formed so that the drop detector probe 19 will activate the circuitry shown in FIG. 7. In general, the drop 33 flows down one of the cell wires 5.

FIG. 5a shows the film 31 held by grounded cell wires 5 running through the lower wire spacer 16 located in the lower body spacer plate 14 containing the overflow detector probe 20.

Figure 8:
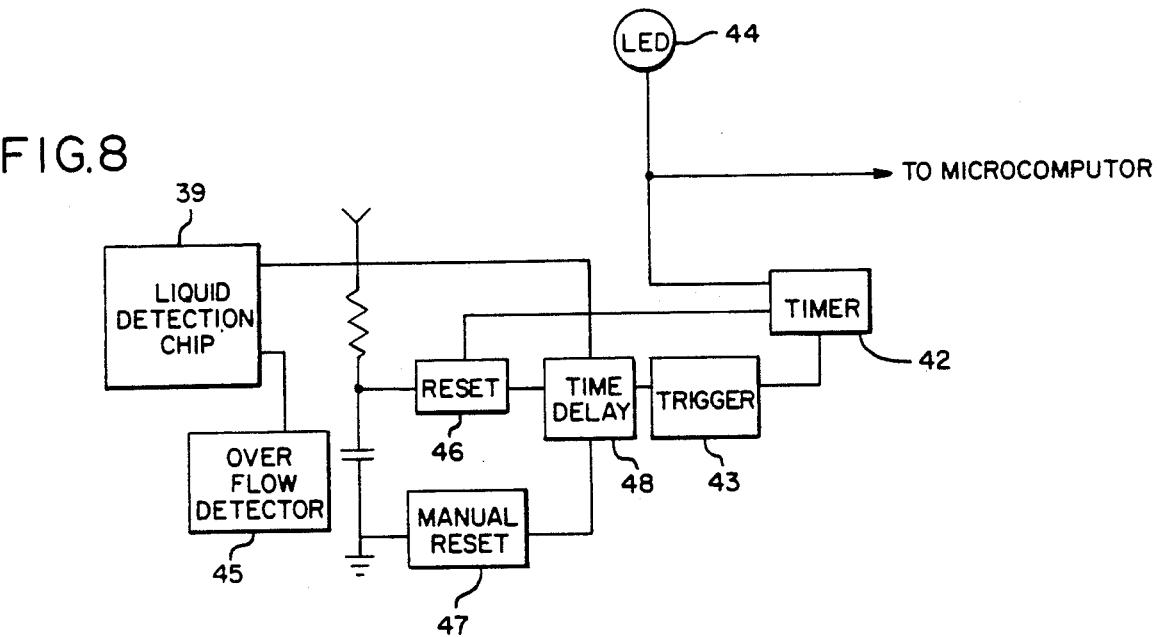
FIG. 8 is a block circuit diagram of the overflow detector probe.

In FIG. 5b, an overflow 77 has occurred resulting in the detection of an overflow condition by the overflow detector probe 20 which in turn activates the circuitry shown in FIG. 8.

FIG. 6 shows a cross section view of the film 31 between the cell wires 5. The minimum film thickness 35 is shown, along with the distance between cell wires 37 and one half the distance between cell wires 36. The cell wire diameter 34 is shown. One half of the additional maximum film thickness 38 is shown.

FIG. 7 shows a block circuit diagram for the drop detector probe 40. A liquid detection chip 39 consisting of a LM 1830 fluid detecting IC chip, provides output to an LED 44 and a trigger chip 43 when the drop detector probe 40 to cell wire capacitance is shorted by a drop 33. The trigger 43 connects to a timer chip 42 and a decade counter chip 41 which in turn is connected to a microcomputer (not shown). The timer chip 42 is also connected to the decade counter chip 41.

FIG. 8 uses another similar liquid detection chip 39 with the overflow detector probe 45 which operates a time-delay circuit 48, trigger chip 43, timer chip 42, and LED 44. Automatic reset 46 is activated with the timer chip 42. The timer chip 42 is connected to a microcomputer (not shown). Also provided is a manual reset button 47.

FIG. 9 is a top view of the micro-volume mixing chamber 58. The mixing chamber top 60 contains a top viewing window 62 through which can be seen the top spacer 66. The main frame 59 is under the mixing chamber top 60. The top spacer 66 is mounted on the mixing chamber top 60.

FIG. 10 is a front cut-away view of the micro-volume mixing chamber 58. The main frame 59 has a hollow cylinder 76 through the center portion. The top 60 is attached to the main frame 59. Similarly, the bottom 61 and mounted bottom spacer 67 are attached to the main frame 59. Top viewing window 62 and bottom viewing window 63 allow viewing throughout the length of the hollow cylinder 76. Side viewing window 64 allows viewing through the side viewing chamber 74. Pressure regulating inlet/outlet 71 is shown within top 60. The cell wires 5 and mixing aid 69 are shown within the hollow cylinder 76. The capillary exit port 70 is shown between cell wires 5 and above bottom spacer 67. Reagent ports 73 are shown.

FIG. 11 is a side view of the micro-volume mixing chamber 58. The front viewing chamber 75 with front viewing window 65 is shown cut into the main frame 59. The full length of the capillary exit port 70 is shown from the cell wires 5 through the bottom 61. The pressure regulating gas inlet/outlet 71 is shown with the primary reagent port 72 within the top 60. Additional reagent ports 73 are shown. Another pressure regulating gas inlet/outlet 71 is positioned near the bottom 61. The use as an inlet or outlet is determined by whether the gas is heavier or lighter than air. Additionally, pressure can be reduced or increased.

FIG. 12 is a detailed view of the top spacer 66. Cell wires 5 are held by cell wire fork 68. Mixing aids 69 are positioned by extending or extracting the pass through rods 78 located in the main frame 59.

FIG. 13 is another embodiment of the cell wires 5 where the cell wires 5 cross and are joined together at geometrically-shaped nodes 84. The geometrically-shaped nodes 84 act as an aid in mixing the reagents by a process similar to an areodynamically-shaped wing.

FIG. 14 shows the spacing from a reagent tube to the cell wire 5. Note the jet stream pulsates and the distance from the end of the reagent tube to the cell wires 5 is about 80% of the period of the emerging jet stream.

In operating the preferred embodiment as a flow cell, a reagent is provided to the primary reagent port 2a by inserting primary reagent tube which forms a film 31 between the cell wires 5. The cell wires 5 are more appropriately called film supports which can be classified as passive film supports which do not interact chemically with the film and active film supports which interact chemically or as a catalyst with the flowing film. The preferred distance 37 between the cell wires 5 is 1.82 millimeters. The examining chamber 49 is 2.5 cm long and the cell wires are 30 gauge wires of nichrome. The film 31 will begin flowing between the two cell wires 5 and through the teflon insert 7. If a secondary reagent and/or a tertiary reagent are used, the reagents flow through the secondary reagent tube 10b and the tertiary reagent tube 11b inserted, respectively, in the secondary reagent port 10a and the tertiary reagent port 11a through the teflon insert 7 and finally onto the cell wires 5 prior to the initiation of flow from the primary tube through the primary reagent port 2a which forms the film 31. The film 31 flows through the examining chamber 49 and through the drop detector probe 19. The lower wire spacer 16 causes the film 31 to divide and flow down each cell wire 5 to the drain cavity 28.

Air is provided to air inlet port 12 which flows through the mid-body plate 9, o-ring 15, lower body spacer plate 14, o-ring 15, and the drain cavity cover 21 into the air inlet cavity 27. Drain port 26 is connected to a low vacuum source which then removes the air and reagent from the air inlet cavity 27 and the drain cavity 28, respectively, through the drain port 26.

The mounting brackets 50 are attached to a photo-multiplier tube housing for continuous flow chemiluminescence measurements.

Referring to FIG. 4b, a condition is shown where the film 31 has not formed and a drop 33 is passing through the drop detector probe 19. Referring now to FIG. 7, the liquid detection chip 39 provides an AC signal to the drop detector probe 19. When a drop 33 passes through the drop detector probes 19, the LED 44 will light. The output of the liquid detection chip 39 is debounced by a Schmidt trigger chip 43 and connected to the input of a decade counter chip 41. The drop 33 passing the drop detector probe 19 will increment the decade counter chip 41. If the count reaches 10 prior to the decade counter reset signal derived from the timer chip 42, a signal will become available at the microcomputer output. The timer chip 42 will automatically reset the decade counter chip 41 after a set time delay.

Referring to FIG. 8 and 5b, the overflow conditions are detected by the liquid detection chip 39 through the overflow detector probe 20. A zero to 15 second time delay is initiated by the time delay circuit 48. At the end of the time delay a pulse triggers the timer chip 42. The timer chip 42 will light the LED 44 and deliver an interrupt pulse to the microcomputer interface. The Schmidt trigger chip 43 is used for signal modifications because debouncing is not required for this circuit.

Referring now to FIGS. 9, 10, 11 and 12, the preferred embodiment of the invention as a micro-volume mixing chamber is shown. A plurality of reagents are transported to the cell wires 5 to form a film by means of a plurality of reagent ports 72 and 73. Mixing aids 69 assist in providing a homogenous mixture of reagents at the capillary exit port 70. The homogenous mixture of reagents may then be transferred to other locations by pump or gravity flow. The hollow cylinder 76 is completely enclosed by top window 62, bottom window 63, side window 64, and front window 65. By the use of pressure regulating gas inlet/outlet 71, the environment of the hollow cylinder 76 may be controlled with respect to pressure and type of gas. Additionally, the type of gas may be reactive or passive similar to the cell wires 5.

Referring to FIG. 13, it is readily apparent the film will flow down the cell wires 5 and be directed to the geometrically-shaped nodes 84 at which point additional mixing of the reagents must occur prior to the formation of film below the geometrically-shaped node 84. The design of the nodes and the number of nodes placed in line will affect the mixing efficiency.

In withdrawing the falling film in either form of the invention, i.e. windowless flow cell or micro-volume mixing chamber, it is sometimes necessary to return the fluid to plug flow condition before analysis at detecting or fraction collecting instrumentation. Plug flow is simply a first in, first out flow. In the windowless flow cell a wettable reagent tube is butted against the falling film 31 and the cell wires 5 at a 90° or greater angle through a reagent port, for example, 55a. Similarly, in the micro-volume mixing chamber, a wettable reagent tube is placed through a reagent port, for example, 73. In both cases, tube confined plug flow results through gravity or vacuum pump.

While the particular invention herein shown and described in detail in two preferred embodiments, it is to be understood that they are merely illustrative of the presently preferred embodiments of the invention and that no limitations are intended to the details of construction or design herein shown other than as defined in the appended claims, which form a part of this disclosure.

We claim:

1. A windowless flow cell comprising:
   a. at least two cell wires fixably fastened and positioned within said windowless flow cell;

b. means for fixably fastening said at least two cell wires;

c. means for fixably positioning said at least two cell wires;

d. means for adding at least one reagent to form a flowing film between said at least two cell wires;

e. an examining chamber through which at least two cell wires pass;

f. means for enclosing said examining chamber; and g. means for withdrawing the at least one reagent from the bottom of said examining chamber.

2. The windowless flow cell of claim 1 wherein
said means for fixably fastening said at least two cell wires comprise: an upper body plate with means defining cell holes from the bottom of said upper body plate to the top of said upper body plate through which said at least two cell wires are contained;

upper body cell wire set screws screwably fastened from the top of said upper body plate to said cell holes frictionally pressing said at least two cell wires against said cell holes where a separate cell hole is provided for each of the at least two cell wires;

a lower body plate with means defining cell holes from the top of said lower body plate to the bottom of said lower body plate through which said at least two cell wires are contained; and lower body cell wire set screws screwably fastened from the bottom of said lower body plate to said cell holes frictionally pressing said at least two cell wires against said cell holes where a separate cell hole is provided for each of the at least two cell wires.

3. The windowless flow cell of claim 1 wherein said means for fixably positioning said at least two cell wires comprise: an upper wire spacer screwably attached to the bottom of an upper body plate where said upper wire spacer contains means defining an opening within which project upper wire spacer prongs positioning said at least two cell wires; and a lower wire spacer frictionally held within a lower body spacer plate where said lower wire spacer contains means defining a clearance hole positioning each said at least two cell wires.

4. The windowless flow cell of claim 1 wherein said means for adding at least one reagent to form a flowing film between said at least two cell wires comprises:
a primary reagent tube located through an upper body plate terminating directly above upper wire spacer prongs and said at least two cell wires.

5. The windowless flow cell of claim 4 additionally comprising: a secondary tube located within a mid body plate and through a teflon insert through means defining a secondary port hole located within said mid body plate;
a tertiary tube located within said mid body plate and through said teflon insert located within said mid body plate through means defining a tertiary port hole located within said mid body plate.

6. The windowless flow cell of claim 5 additionally comprising: a means for adjusting spacing between the secondary and tertiary port holes and said at least two cell wires.

7. The windowless flow cell of claim 1 wherein said means for enclosing said examining chamber comprise:
a mid body plate fixably attached to lower body spacer plate into which a mirror block is slidably fixed; and where the front of said mid body plate is fixably attachable to an examining instrument.

8. The windowless flow cell of claim 1 wherein said means for withdrawing the at least one reagent comprise:
an air inlet port within a mid body plate which communicates through an o-ring through a lower body spacer plate which in turn communicates through another o-ring and through a drain cavity cover to an air inlet cavity;
a lower wire spacer with means defining clearance holes through which the film flows down said cell wires to a drain cavity; and
said air inlet cavity and said drain cavity communicate with a drain port attached to a vacuum pump.

9. The windowless flow cell of claim 8 wherein the means for withdrawing the at least one reagent additionally comprises: at least one wettable reagent tube communicating with the flowing film at an angle of at least 90 degrees.

10. The windowless flow cell of claim 1 additionally comprising: a drop detector probe positioned near said at least two cell wires above a lower body spacer plate interconnected to a liquid detection chip, an LED, a trigger, a decade counter, a timer and a microcomputer.

11. The windowless flow cell of claim 1 additionally comprising: an overflow detector probe positioned near said at least two cell wires above a lower body spacer plate interconnected to a liquid detection chip, a time delay, a reset, a trigger, a timer, an LED, and a microcomputer.

12. A micro-volume mixing chamber comprising:
a. at least two cell wires fixably fastened and positioned within said micro-volume mixing chamber;
b. means for fixably fastening said at least two cell wires;
c. means for fixably positioning said at least two cell wires;
d. means for adding at least one reagent to form a flowing film between said at least two cell wires;
e. a hollow chamber within a mainframe through which said at least two cell wires pass; and
f. means for withdrawing the at least one reagent from said hollow chamber.

13. The micro-volume mixing chamber of claim 12 where said means for withdrawing the at least one reagent comprise:
a capillary exit port located between said at least two cell wires above a bottom spacer and communicating to the outside of said micro-volume mixing chamber.

14. The micro-volume mixing chamber of claim 13 wherein the means for withdrawing the at least one reagent additionally comprises:
at least one wettable reagent tube communicating with a flowing film at an angle of at least 90 degrees.

15. The micro-volume mixing chamber of claim 12 additionally comprising:
a top and bottom of said mainframe; and at least one pressure regulating gas inlet/outlet communicating with said hollow chamber.

16. The micro-volume mixing chamber of claim 15 additionally comprising at least one window to said hollow chamber.

17. The micro-volume mixing chamber of claim 12 additionally comprising at least one adjustable mixing aid perpendicular to a flowing film in said hollow chamber.

18. The micro-volume mixing chamber of claim 12 where said means for adding at least one reagent to from a flowing film between said at least two cell wires additionally comprises a means for adjusting the spacing between the at least one reagent and said at least two cell wires.

* * * * *